(12) United States Patent
Nishijima

(10) Patent No.: US 12,181,616 B2
(45) Date of Patent: Dec. 31, 2024

(54) RADIATION DETECTOR MODULE, RADIATION DETECTOR, AND X-RAY CT APPARATUS

(71) Applicant: CANON MEDICAL SYSTEMS CORPORATION, Otawara (JP)

(72) Inventor: Akira Nishijima, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 360 days.

(21) Appl. No.: 17/717,563

(22) Filed: Apr. 11, 2022

(65) Prior Publication Data

US 2022/0334267 A1     Oct. 20, 2022

(30) Foreign Application Priority Data

Apr. 14, 2021   (JP) ................................ 2021-068406
Feb. 25, 2022   (JP) ................................ 2022-028531

(51) Int. Cl.
*G01T 1/16*     (2006.01)
*A61B 6/03*     (2006.01)
*A61B 6/42*     (2024.01)

(52) U.S. Cl.
CPC ............... *G01T 1/16* (2013.01); *A61B 6/032* (2013.01); *A61B 6/4233* (2013.01)

(58) Field of Classification Search
CPC ..................................................... G01T 1/243
See application file for complete search history.

(56) References Cited

U.S. PATENT DOCUMENTS

| 6,657,180 B1* | 12/2003 | Monnet ............. H01L 27/14658 |
| | | 250/214 R |
| 2009/0290680 A1 | 11/2009 | Tümer et al. |
| 2010/0116999 A1 | 5/2010 | Tümer et al. |
| 2010/0255629 A1 | 10/2010 | Spartiotis et al. |
| 2012/0090171 A1 | 4/2012 | Spartiotis et al. |
| 2012/0193545 A1* | 8/2012 | Tkaczyk ............... G01T 1/2928 |
| | | 250/370.08 |
| 2017/0052263 A1 | 2/2017 | Jadrich et al. |
| 2017/0153334 A1 | 6/2017 | Jadrich et al. |

FOREIGN PATENT DOCUMENTS

| JP | 2009-018154 A | 1/2009 |
| JP | 2009-076690 A | 4/2009 |
| JP | 2011-085479 A | 4/2011 |

OTHER PUBLICATIONS

Extended European Search Report issued Jul. 22, 2022 in European Patent Application No. 22167931.9, citing documents 1 through 3 therein, 7 pages.

* cited by examiner

*Primary Examiner* — Hoon K Song
(74) *Attorney, Agent, or Firm* — Oblon, McClelland, Maier & Neustadt, L.L.P.

(57) ABSTRACT

A radiation detector module of an embodiment includes a radiation detector, a first electrode, a second electrode, and a mark. The radiation detector includes an incident surface and is configured to detect radiation incident from the incident surface. The first electrode is provided on the side of the incident surface of the radiation detector. The second electrode is provided to face the first electrode through the radiation detector. The mark is provided on at least one of the incident surface of the radiation detector and the first electrode.

11 Claims, 11 Drawing Sheets

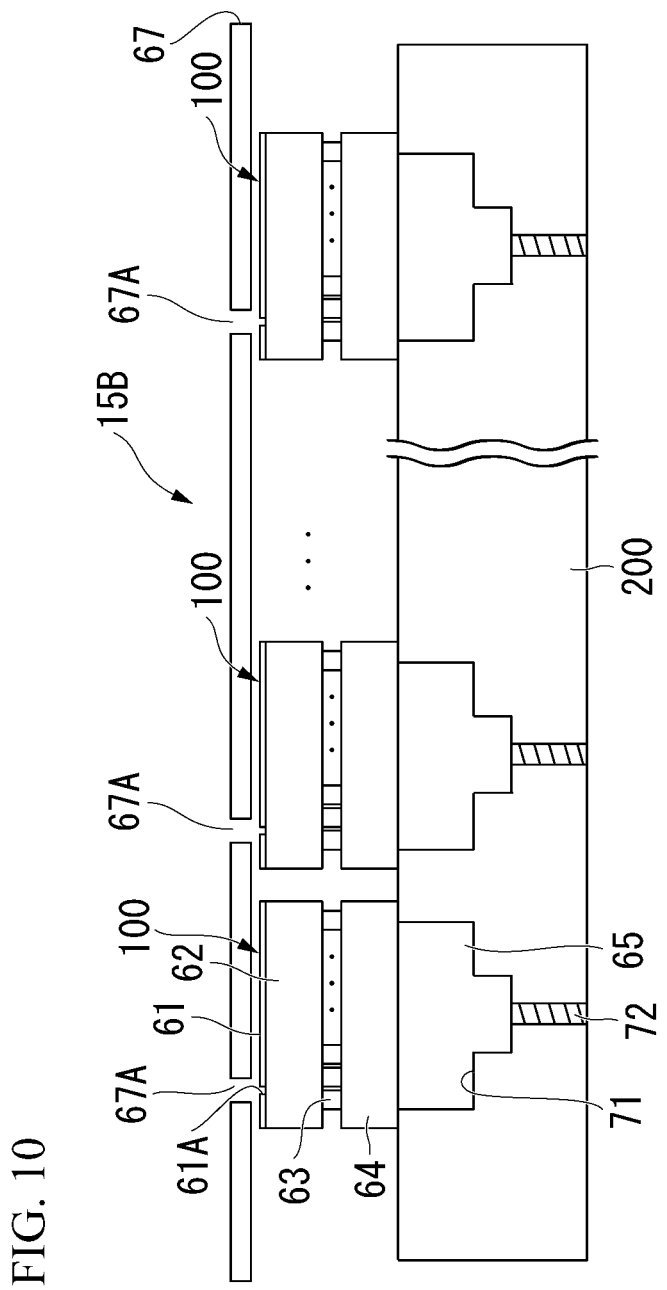

RADIATION DETECTOR MODULE, RADIATION DETECTOR, AND X-RAY CT APPARATUS

CROSS-REFERENCE TO RELATED APPLICATION

The present application claims priority based on Japanese Patent Application No. 2021-068406 filed Apr. 14, 2021 and Japanese Patent Application No. 2022-028531 filed Feb. 25, 2022, the contents of which are incorporated herein by reference.

FIELD

Embodiments disclosed in the present description and drawings relate to a radiation detector module, a radiation detector, and an X-ray CT apparatus.

BACKGROUND

A plurality of radiation detector modules are arranged side by side in a radiation detector. When radiation is detected by a plurality of radiation detector modules arranged side by side, the accuracy of positioning of the radiation detector modules has a great influence on the detection accuracy of the radiation detector. Positioning of radiation detector modules has been performed, for example, on the basis of pins provided on a mounting part of the radiation detector modules.

However, it is difficult to improve the accuracy of positioning based on the pins. In particular, the detection accuracy of a radiation detector is greatly affected by the relative positional relationship between radiation detector modules arranged side by side. However, since positioning based on the pins does not directly adjust the positional relationship between radiation detector modules, it is difficult to improve the positioning accuracy of the radiation detector modules.

BRIEF DESCRIPTION OF THE DRAWINGS

FIG. 10 is an enlarged view showing a part of an X-ray detector unit 15B according to a third embodiment.

DETAILED DESCRIPTION

Hereinafter, a radiation detector module, a radiation detector, and an X-ray CT apparatus of embodiments will be described with reference to the drawings.

A problem to be solved by the embodiments disclosed in the present description and the drawings is to improve the positioning accuracy of radiation detector modules. However, the problems to be solved by the embodiments disclosed in the present description and the drawings are not limited to the above problem. It is also possible to regard a problem corresponding to each effect according to each configuration illustrated in an embodiment which will be described later as another problem.

A radiation detector module of an embodiment includes a radiation detector, a first electrode, a second electrode, and a mark. The radiation detector includes an incident surface and is configured to detect radiation incident from the incident surface. The first electrode is provided on the side of the incident surface of the radiation detector. The second electrode is provided to face the first electrode through the radiation detector. The mark is provided on at least one of the incident surface of the radiation detector and the first electrode.

First Embodiment

Figure 1:
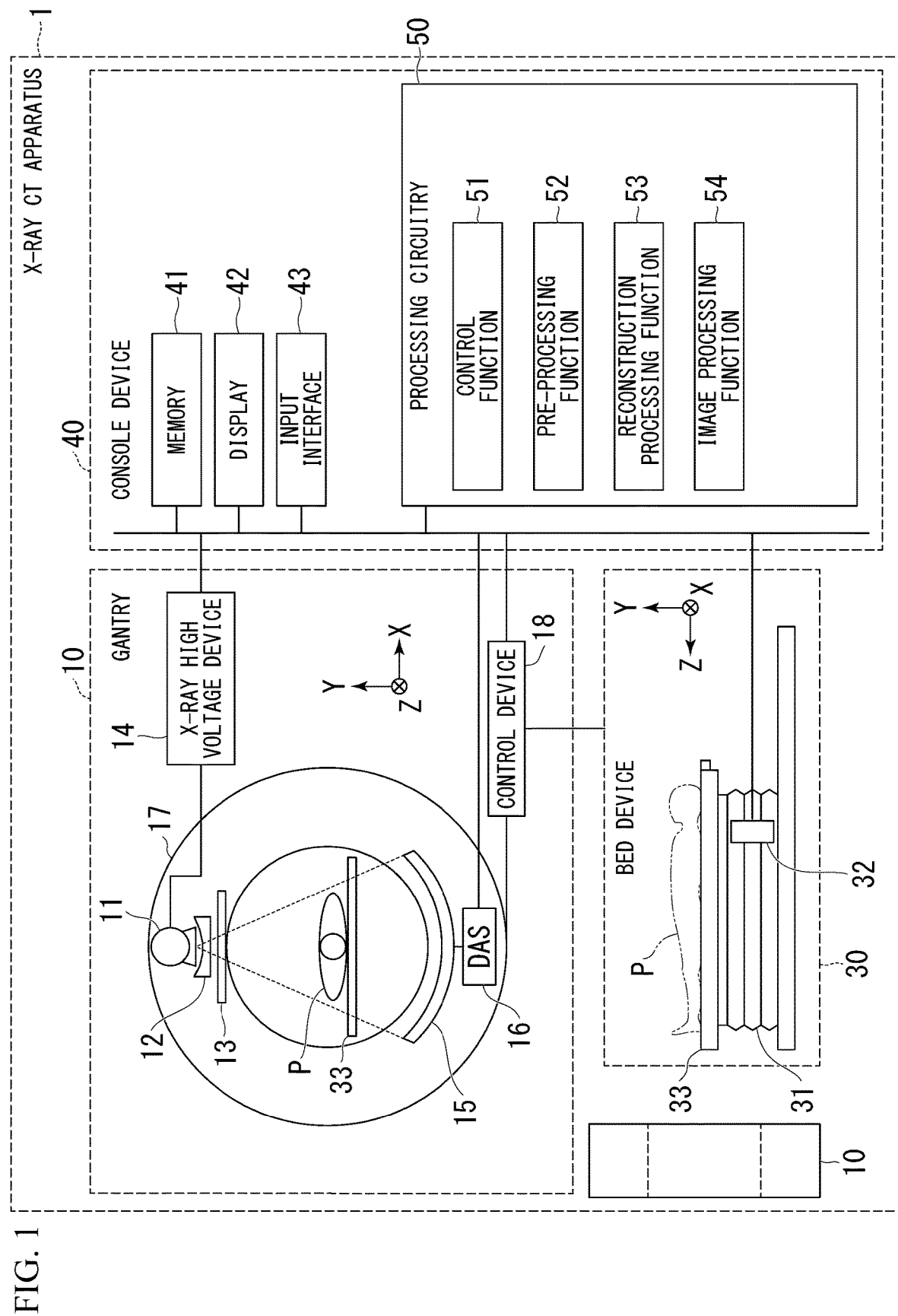
FIG. 1 is a configuration diagram of an X-ray CT apparatus 1 according to a first embodiment.

FIG. 1 is a configuration diagram of an X-ray CT apparatus 1 according to an embodiment. The X-ray CT device 1 includes, for example, a gantry 10, a bed device 30, and a console device 40. Although FIG. 1 shows both a view of the gantry 10 from a Z-axis direction and a view from an X-axis direction for convenience of description, there is one gantry 10 in reality. In the embodiment, a rotation shaft of a rotary frame 17 in a non-tilt state or the longitudinal direction of a top plate 33 of the bed device 30 is defined as the Z-axis direction, an axis orthogonal to the Z-axis direction and horizontal to the floor surface is defined as the X-axis direction, and a direction orthogonal to the Z-axis direction and perpendicular to the floor surface is defined as a Y-axis direction. The X-ray CT apparatus 1 captures a contrast-enhanced CT image for performing imaging examination.

The gantry 10 includes, for example, an X-ray tube 11, a wedge 12, a collimator 13, an X-ray high voltage device 14, an X-ray detector 15, a data acquisition system (hereinafter, DAS) 16, the rotary frame 17, and a control device 18.

The X-ray tube 11 generates X-rays by radiating thermions from a cathode (filament) toward an anode (target) when a high voltage from the X-ray high voltage device 14 is applied thereto. The X-ray tube 11 includes a vacuum tube. For example, the X-ray tube 11 is a rotating anode type X-ray tube that generates X-rays by radiating thermions to a rotating anode.

The wedge 12 is a filter for adjusting an X-ray dose radiated from the X-ray tube 11 to a subject P that is an imaging examination target. The wedge 12 attenuates X-rays passing therethrough such that the distribution of the X-ray dose applied to the subject P from the X-ray tube 11 becomes a predetermined distribution. The wedge 12 is also called a wedge filter or a bow-tie filter. The wedge 12 is made by processing aluminum so as to have a predetermined target angle and a predetermined thickness, for example.

The collimator 13 is a mechanism for narrowing the radiation range of X-rays that have passed through the wedge 12. The collimator 13 narrows the radiation range of X-rays by forming a slit, for example, according to combination of a plurality of lead plates. The collimator 13 may be called an X-ray diaphragm. A narrowing range of the collimator 13 may be mechanically driven.

The X-ray high voltage device 14 includes, for example, a high voltage generation device and an X-ray control device. The high voltage generation device has an electric circuit including a transformer, a rectifier, and the like and generates a high voltage applied to the X-ray tube 11. The X-ray control device controls an output voltage of the high voltage generation device according to the X-ray dose to be generated in the X-ray tube 11. The high voltage generation device may boost the voltage by the transformer described above or boost the voltage by an inverter. The X-ray high voltage device 14 may be provided on the rotary frame 17 or may be provided on the side of a fixed frame (not shown) of the gantry 10.

The X-ray detector 15 detects the intensity of X-rays generated by the X-ray tube 11, passed through the subject P and incident thereon. The X-ray detector 15 outputs an electrical signal (which may be an optical signal or the like) depending on the intensity of the detected X-rays to the DAS 16. The X-ray detector 15 is, for example, a so-called photon counting detector that counts photons to measure X-rays. The X-ray detector 15 may be a scintillator. The X-ray detector 15 is an example of a radiation detector. The detailed configuration of the X-ray detector 15 will be described later.

The DAS 16 includes, for example, an amplifier, an integrator, and an A/D converter. The amplifier performs amplification processing on an electrical signal output from each X-ray detection element of the X-ray detector 15. The integrator integrates the amplified electrical signal over a view period. The A/D converter converts an electrical signal indicating the integration result into a digital signal. The DAS 16 outputs detection data based on the digital signal to the console device 40.

The rotary frame 17 is an annular rotating member that rotates the X-ray tube 11, the wedge 12, the collimator 13, and the X-ray detector 15 while holding them facing each other. The rotary frame 17 is rotatably supported by the fixed frame around the subject P introduced inside. The rotary frame 17 further supports the DAS 16. The detection data output from the DAS 16 is transmitted from a transmitter having light-emitting diodes (LEDs) provided in the rotary frame 17 to a receiver having photodiodes provided in a non-rotating part (for example, the fixed frame) of the gantry 10 according to optical communication and transferred to the console device 40 by the receiver. A method of transmitting the detection data from the rotary frame 17 to the non-rotating part is not limited to the above-mentioned method using optical communication, and any non-contact transmission method may be adopted. The rotary frame 17 is not limited to an annular member as long as it can support and rotate the X-ray tube 11 and the like and may be a member such as an arm.

Although the X-ray CT apparatus 1 may be, for example, a rotate/rotate-type X-ray CT apparatus (third-generation CT) in which both the X-ray tube 11 and the X-ray detector 15 are supported by the rotary frame 17 and rotate around the subject P, the X-ray CT apparatus 1 is not limited to this and may be a stationary/rotate-type X-ray CT apparatus (fourth-generation CT) in which a plurality of X-ray detection elements arranged in an annular shape are fixed to a fixed frame and the X-ray tube 11 rotates around the subject P.

The control device 18 includes, for example, processing circuitry having a processor such as a central processing unit (CPU) and a drive mechanism including a motor, an actuator, and the like. The processing circuitry realizes these functions by, for example, a hardware processor executing a program stored in a storage device (storage circuit).

The hardware processor means, for example, a circuit (circuitry) such as a central processing unit (CPU), a graphics processing unit (GPU), an application specific integrated circuit (ASIC), a programmable logic device (for example, a simple programmable logic device (SPLD) or a complex programmable logic device (CPLD)), and a field programmable gate array (FPGA). The program may be configured to be directly embedded in the circuit of the hardware processor instead of being stored in a storage device. In this case, the hardware processor realizes functions by reading and executing the program embedded in the circuit. The hardware processor is not limited to a configuration as a single circuit and may be configured as one hardware processor by combining a plurality of independent circuits to realize respective functions. The storage device may be a non-transitory (hardware) storage medium. Further, a plurality of components may be integrated into one hardware processor to realize respective functions.

The control device 18 rotates the rotary frame 17, tilts the gantry of the gantry 10, moves the top plate 33 of the bed device 30 according to vertical movement, or the like, and causes X-rays to be radiated (allow exposure) from the X-ray tube 11, for example. The control device 18 may be provided in the gantry 10 or the console device 40.

The bed device 30 is a device on which the subject P to be scanned is placed and introduced into the rotary frame 17 of the gantry 10. The bed device 30 includes, for example, a base 31, a bed driving device 32, the top plate 33, and a support frame 34. The base 31 includes a housing that movably supports the support frame 34 in the vertical direction (Y-axis direction). The bed driving device 32 includes a motor and an actuator. The bed driving device 32 moves the top plate 33 on which the subject P is placed along the support frame 34 in the longitudinal direction (Z-axis direction) of the top plate 33. The top plate 33 is a plate-shaped member on which the subject P is placed.

The console device 40 includes, for example, a memory 41, a display 42, an input interface 43, and processing circuitry 50. In the embodiment, the console device 40 will be described as a separate body from the gantry 10, but the gantry 10 may include a part or all of components of the console device 40.

The memory 41 is realized by, for example, a semiconductor memory element such as a random access memory (RAM) and a flash memory, a hard disk, an optical disc, or the like. The memory 41 stores, for example, detection data, projection data, reconstructed image data, CT image data, and the like. Such data may be stored in an external memory with which the X-ray CT apparatus 1 can communicate instead of the memory 41 (or in addition to the memory 41). The external memory is controlled by, for example, a cloud server that manages the external memory upon reception of a read/write request by the cloud server.

The display 42 displays various types of information. For example, the display 42 displays a medical image (CT image) generated by the processing circuitry, a graphical user interface (GUI) image through which various operations by an operator such as a doctor or a technician are received, and the like. The display 42 is, for example, a liquid crystal display, a cathode ray tube (CRT), an organic electroluminescence (EL) display, or the like. The display 42 may be provided on the gantry 10. The display 42 may be a desktop type or a display device (for example, a tablet terminal) capable of wirelessly communicating with the main body of the console device 40.

The input interface 43 receives various input operations of the operator and outputs an electrical signal indicating details of the received input operations to the processing circuitry 50. For example, the input interface 43 receives input operations such as collection conditions at the time of collecting detection data or projection data, reconstruction conditions at the time of reconstructing a CT image, and image processing conditions at the time of generating a post-processed image from a CT image.

The input interface 43 is realized by, for example, a mouse, a keyboard, a touch panel, a drag ball, a switch, a button, a joystick, a camera, an infrared sensor, a microphone, or the like. The input interface 43 may be realized by a display device (for example, a tablet terminal) capable of wirelessly communicating with the main body of the console device 40.

In the present description, the input interface is not limited to the one provided with physical operation parts such as a mouse and a keyboard. For example, examples of the input interface also include electrical signal processing circuitry that receives an electrical signal corresponding to an input operation from an external input apparatus provided separately from the device and outputs the electrical signal to the control circuit.

The processing circuitry 50 controls the overall operation of the X-ray CT apparatus 1. The processing circuitry 50 includes, for example, a control function 51, a pre-processing function 52, a reconstruction processing function 53, and an image processing function 54. The processing circuitry 50 realizes these functions by, for example, a hardware processor executing a program stored in a storage device (storage circuit).

The hardware processor means, for example, a circuit such as a CPU, a GPU, an application specific integrated circuit, a programmable logic device or a complex programmable logic device, and a field programmable gate array. The program may be configured to be directly embedded in the circuit of the hardware processor instead of being stored in the storage device. The hardware processor is not limited to a configuration as a single circuit and may be configured as one hardware processor by combining a plurality of independent circuits to realize respective functions. The storage device may be a non-transitory (hardware) storage medium. Further, a plurality of components may be integrated into one hardware processor to realize respective functions.

Each component of the console device 40 or the processing circuitry 50 may be decentralized and realized by a plurality of hardware circuits. The processing circuitry 50 may be realized by a processing device capable of communicating with the console device 40 instead of being a component included in the console device 40. The processing device is, for example, a workstation connected to one X-ray CT apparatus or a device (for example, a cloud server) connected to a plurality of X-ray CT apparatuses and collectively executing the same processing as that of the processing circuitry 50 which will be described below. Each function included in the processing circuitry 50 may be distributed to a plurality of circuits or may be made available by activating application software stored in the memory 41.

The control function 51 controls various functions of the processing circuitry 50 on the basis of input operations received by the input interface 43. The pre-processing function 52 performs pre-processing such as logarithmic conversion processing, offset correction processing, inter-channel sensitivity correction processing, and beam hardening correction on detection data output from DAS 16 to generate projection data and stores the generated projection data in the memory 41.

The reconstruction processing function 53 performs reconstruction processing on the projection data generated by the pre-processing function 52 by a filter correction back projection method, a successive approximation reconstruction method, or the like to generate CT image data and stores the generated CT image data in the memory 41.

The image processing function 54 converts the CT image data into three-dimensional image data or cross-sectional image data with an arbitrary cross section by a known method on the basis of an input operation received by the input interface 43. Conversion into the three-dimensional image data may be performed by the pre-processing function 52.

Figure 2:
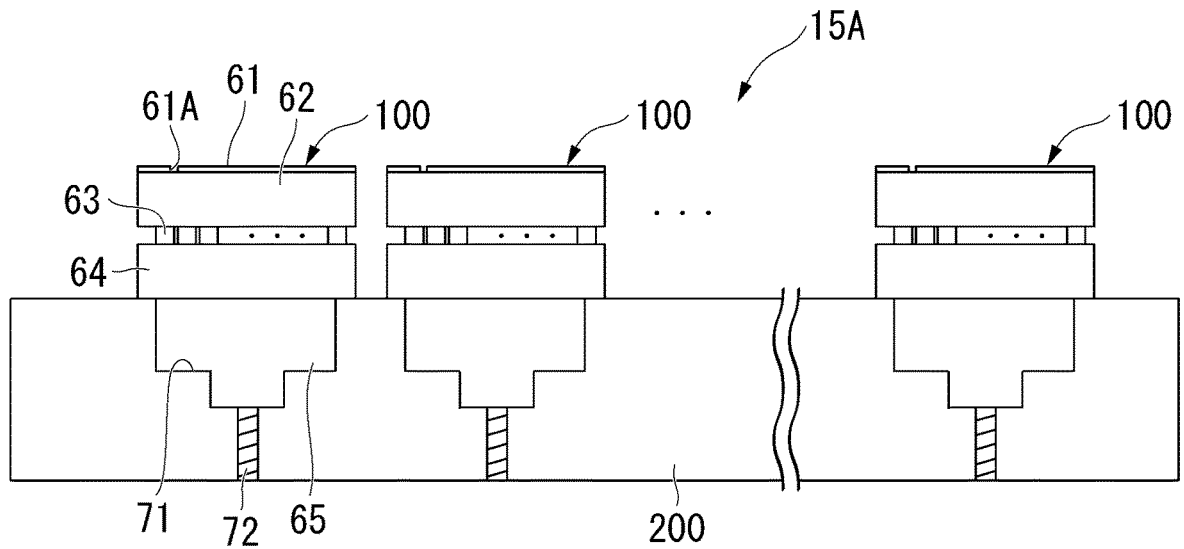
FIG. 2 is an enlarged view showing a part of an X-ray detector unit 15A according to the first embodiment.

Subsequently, the configuration of the X-ray detector 15 will be described. The X-ray detector 15 is provided by arranging a plurality of X-ray detector units 15A side by side. FIG. 2 is an enlarged view showing a part of the X-ray detector unit 15A. The X-ray detector unit 15A includes, for example, a plurality of radiation detector modules (hereinafter, detector modules) 100 and a positioning plate 200. The plurality of detector modules 100 are arranged in a row and fixed to the positioning plate 200. The plurality of detector modules 100 are positioned such that their positions relative to each other can be adjusted. The detector modules 100 are an X-ray detection element array.

Each detector module 100 includes, for example, a first electrode 61, a detection element 62, a second electrode 63, a substrate layer 64, and a mounting member 65. In the following description, the side of the detector module 100 on which the first electrode 61 is provided may be referred to as an upper side and the side on which the second electrode 63 is provided may be referred to as a lower side.

The first electrode 61 is provided on the surface side (upper side) of the detection element 62. The first electrode 61 is a high voltage (HV) electrode having a higher potential than that of the second electrode 63. The first electrode 61 is formed, for example, by depositing a metal material on the surface of the detection element 62. The first electrode 61 may be formed by a method other than vapor deposition.

The detection element 62 is formed of, for example, CdTe or CZT. The detection element 62 detects radiation incident from an incident surface on the surface side of the detector module 100. The plurality of detector modules 100 are provided, for example, by being linearly arranged on the positioning plate 200 having a substantially rectangular parallelepiped outer shape. The detection element 62 is an example of a radiation detection element.

The second electrode 63 is provided on the back surface of the detection element 62. The second electrode 63 is provided such that it faces the first electrode 61 with the detection element 62 interposed therebetween. The second electrode 63 is a low voltage (LV) electrode. By energizing the first electrode 61 and the second electrode 63, radiation is detected by the detection element 62.

The substrate layer 64 is provided on the back surface side of the second electrode 63. The substrate layer 64 supports the first electrode 61, the detection element 62, and the second electrode 63. The substrate layer 64 includes, for example, a support substrate. Electrical elements such as IC chips are attached to the support substrate. The electrical elements are connected through, for example, a wiring cable.

The mounting member 65 is housed in a plurality of positioning holes 71 formed in the positioning plate 200 and is fixed to the positioning plate by a screw 72. The substrate layer 64 is fixed to the mounting member 65 with a screw or the like that is not shown. By fixing the substrate layer 64 to the mounting member 65, the detector module 100 is fixed to the positioning plate 200.

Figure 3:
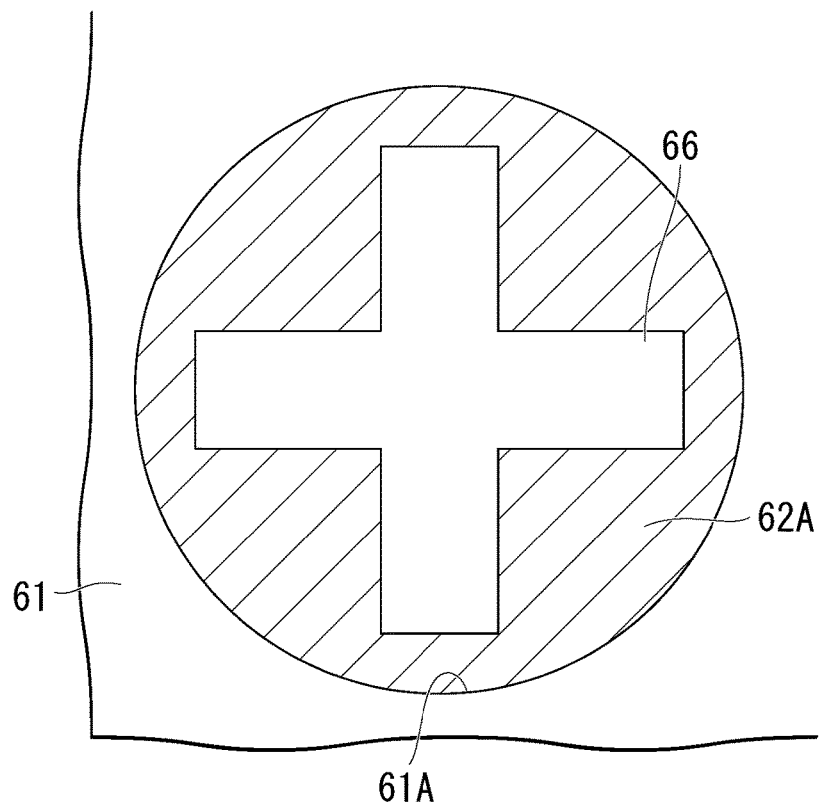
FIG. 3 is a diagram showing a surface of a detection element 62 when a through hole 61A according to the first embodiment is viewed from above.

Further, a through hole 61A is formed in the first electrode 61. A part of the surface of the detection element 62 is exposed at the portion where the through hole 61A is formed. When the through hole 61A is viewed from above the first electrode 61, the exposed portion on the surface of the detection element 62 can be visually recognized. FIG. 3 is a diagram showing the surface of the detection element 62 when the through hole 61A is viewed from above.

A mark 66 is provided on the exposed portion on the surface of the detection element 62. The mark 66 includes, for example, a portion formed by covering the entire surface of the detection element 62 seen through the through hole 61A with the same material as the first electrode 61 and hollowing out the central portion thereof. The mark 66 is formed by masking the portion of the surface of the detection element 62 seen through the through hole 61A, on which the mark 66 will be formed, at the time of vapor-depositing the metal to form the first electrode 61. The mark 66 has a bordering portion 62A that borders the mark 66, formed on the surface of the detection element 62 seen through the through hole 61A.

Figure 4:
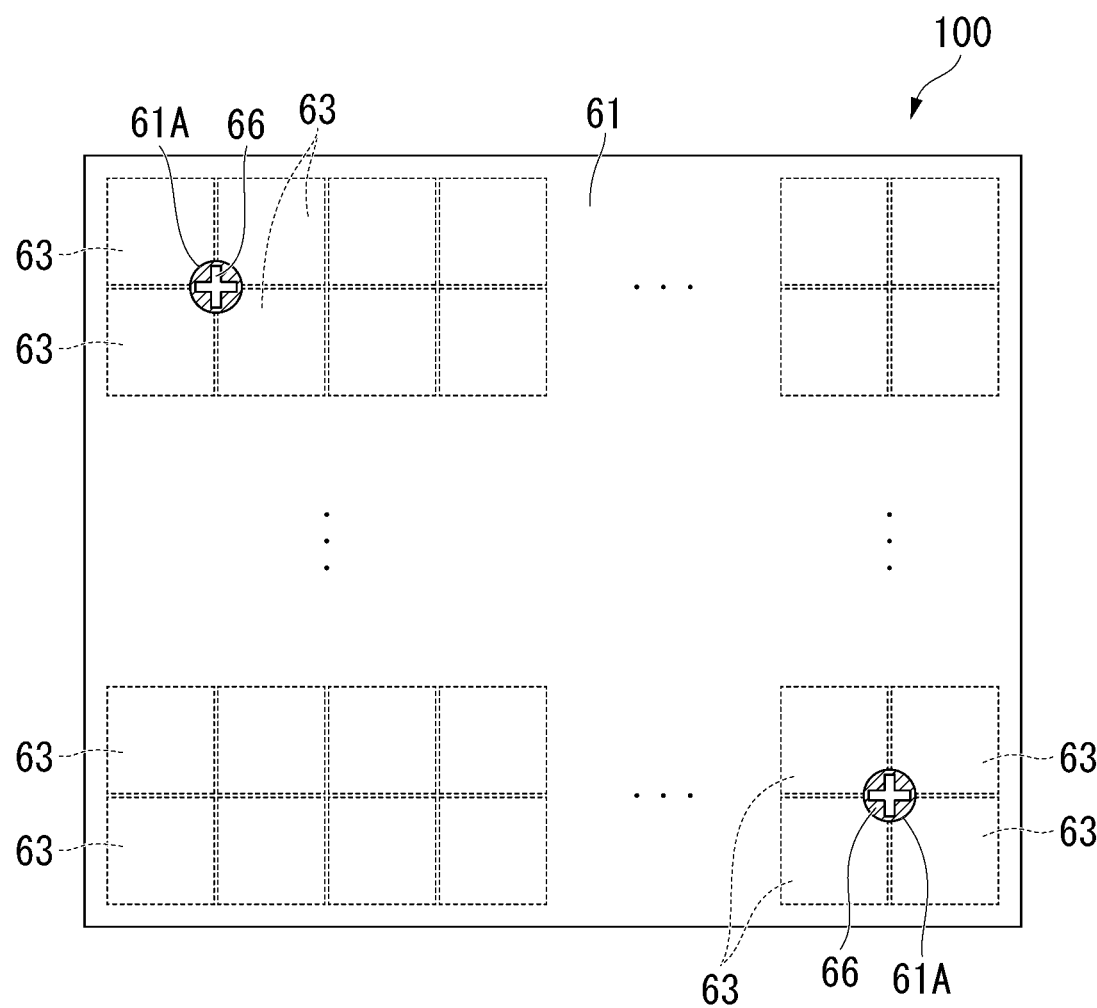
FIG. 4 is a diagram showing a state in which a detector module 100 according to the first embodiment is viewed from above.

FIG. 4 is a diagram showing a state in which the detector module 100 is viewed from above. The detector module 100 is provided with, for example, a plurality of second electrodes 63. The second electrodes 63 all have substantially the same rectangular shape when viewed from above. The plurality of second electrodes 63 are arranged in a matrix. One pixel is configured for one second electrode 63.

Two through holes 61A are formed in the first electrode 61 such that they face corners where four second electrodes 63 at diagonal positions of the first electrode 61 among the plurality of second electrodes 63 arranged in a matrix face each other. The mark 66 is provided on both portions of the surface of the detection element 62 seen through the two through holes 61A. The mark 66 is provided at a plurality of places (two places in the first embodiment) on the surface of the detection element 62. The through holes 61A are provided only at positions where the mark 66 can be visually recognized from the incident surface side. The through holes 61A may be provided at positions other than the positions where the mark 66 can be visually recognized from the incident surface side.

Figure 5:
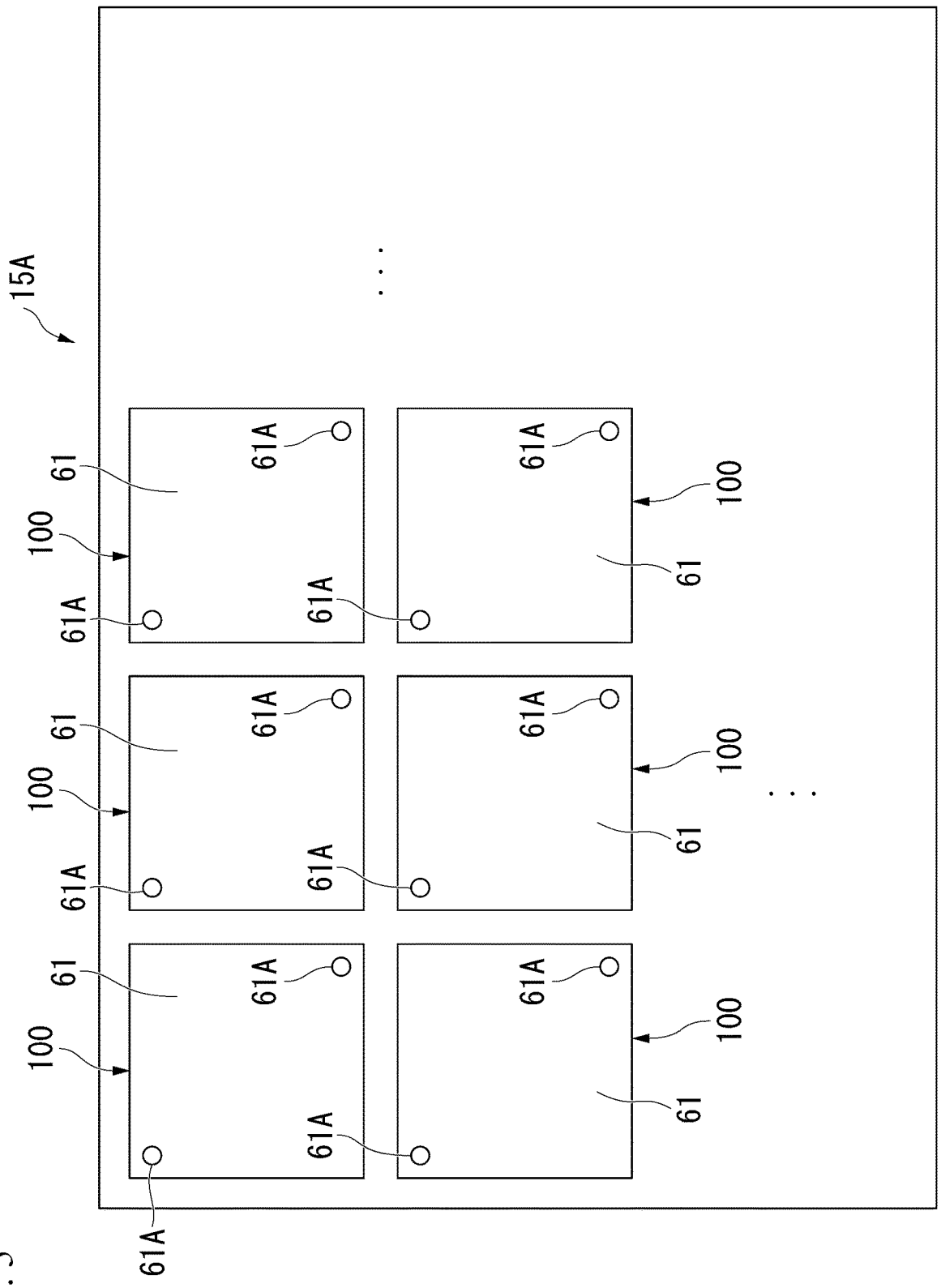
FIG. 5 is a diagram of the X-ray detector unit 15A according to the first embodiment when viewed from above.

FIG. 5 is a view of the X-ray detector unit 15A when viewed from above. The plurality of detector modules 100 are arranged side by side in the X-ray detector unit 15A. Two through holes 61A are formed in each of the plurality of detector modules 100, and the mark 66 (refer to FIG. 3) is provided at positions seen through the through holes 61A. By aligning the positions of the marks 66 seen from the through holes 61A between adjacent detector modules 100, the adjacent detector modules 100 are positioned with respect to each other.

The mark 66 is provided on the basis of the positions of the second electrodes 63. The mark 66 is provided, for example, to position the plurality of detector modules 100 such that pixels of adjacent detector modules 100 are arranged in an orderly manner. Since the pixels in the detector modules 100 are based on the positions and range of the second electrodes 63, the mark 66 is used to align the second electrodes 63 with the second electrodes 63 in another adjacent detector module 100.

Next, a manufacturing procedure of the detector module 100 will be described, and then a manufacturing procedure of the X-ray detector unit 15A will be described. At the time of manufacturing the detector module 100, the substrate layer 64 is manufactured first, and the second electrode 63 is manufactured on the surface of the substrate layer 64 by, for example, vapor deposition. Subsequently, the detection element 62 is formed on the surface of the second electrode 63.

After formation of the detection element 62, the first electrode 61 is formed by depositing a metal to be the first electrode 61 on the surface of the detection element 62. At the time of depositing the metal to be the first electrode 61, portions to be the through holes 61A and portions to be the marks 66 are masked. In this manner, the marks 66 bordered by the bordering portions 62A formed of the same material as the first electrode 61 is formed. The layer of the first electrode 61 may be formed after formation of the layer of the bordering portions 62A and the marks 66. The through holes 61A may be formed by depositing a metal to be the first electrode 61 on the overall surface of the detection element 62 and then performing etching preprocess or the like.

Figure 6:
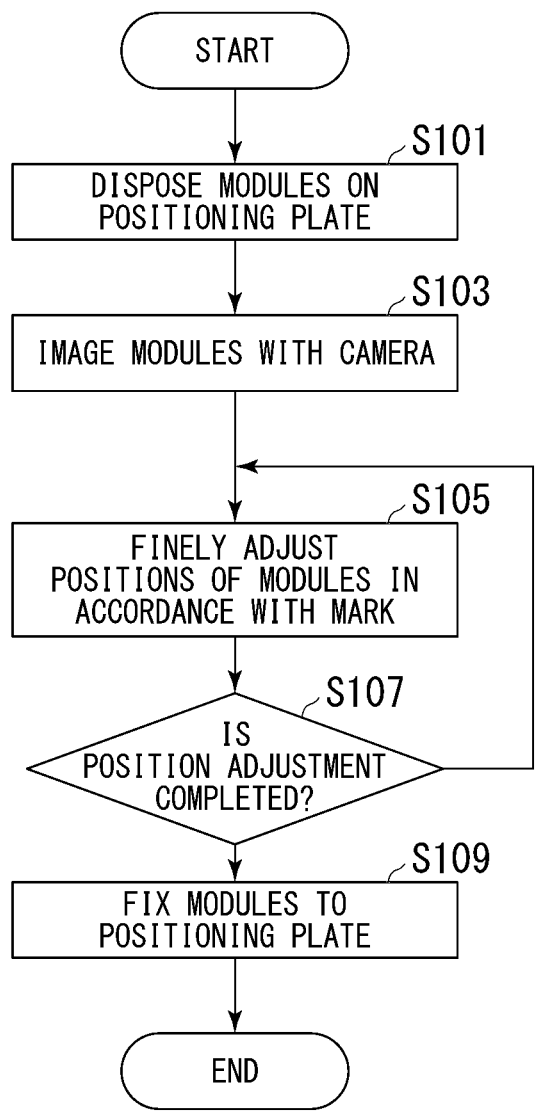
FIG. 6 is a flowchart showing a process of manufacturing the X-ray detector unit 15A according to the first embodiment.

Next, a procedure for manufacturing the X-ray detector unit 15A will be described. FIG. 6 is a flowchart showing an example of a manufacturing procedure of the X-ray detector unit 15A. At the time of manufacturing the X-ray detector unit 15A, first, the assembled detector modules 100 are grasped by, for example, a robot hand and disposed on the positioning plate 200 (step S101). In this state, the detector modules 100 are not yet fixed to the positioning plate 200.

Subsequently, the detector modules 100 are imaged by a camera from above (step S103), and the camera transmits the captured image to a control device that is not shown. The control device analyzes the transmitted image and sets the position of each detector module 100 on the basis of the positions of the marks 66 provided on each of the plurality of detector modules 100 in the image. The control device controls the robot hand on the basis of the set position of each detector module 100 and finely adjusts the positions of adjacent detector modules 100 (step S105).

Subsequently, after finely adjusting the positions of the detector modules 100, the detector modules 100 are additionally imaged with the camera from above and the positions of the detector modules 100 are adjusted on the basis of the marks 66 provided on each of the plurality of detector modules 100 in the image. In position adjustment of the detector modules 100, the marks 66 of adjacent detector modules 100 are aligned, and further, the second electrodes 63 are aligned. Subsequently, the control device determines whether or not position adjustment of the detector modules 100 is completed (step S107). If it is determined that position adjustment of the detector modules 100 is not completed, the procedure returns to step S105 and the positions of the detector modules 100 are finely adjusted.

When it is determined that position adjustment of the detector modules 100 is completed, the detector modules 100 are fixed to the positioning plate 200 by fixing the detector modules 100 to the mounting member 65 and fixing the mounting member 65 to the positioning plate 200 by the screw 72 (step S109). In this manner, manufacturing of the X-ray detector unit 15A is completed.

In the detector modules 100 of the first embodiment, the mark 66 for aligning pixels between adjacent detector module 100 is provided on the detection element 62. The first electrode 61 is provided with the through hole 61A that allows the mark 66 provided on the detection element 62 to be visually recognizable. Accordingly, positioning is performed while viewing the mark 66, and thus the accuracy of positioning of the detector modules 100 can be improved.

Second Embodiment

Figure 7:
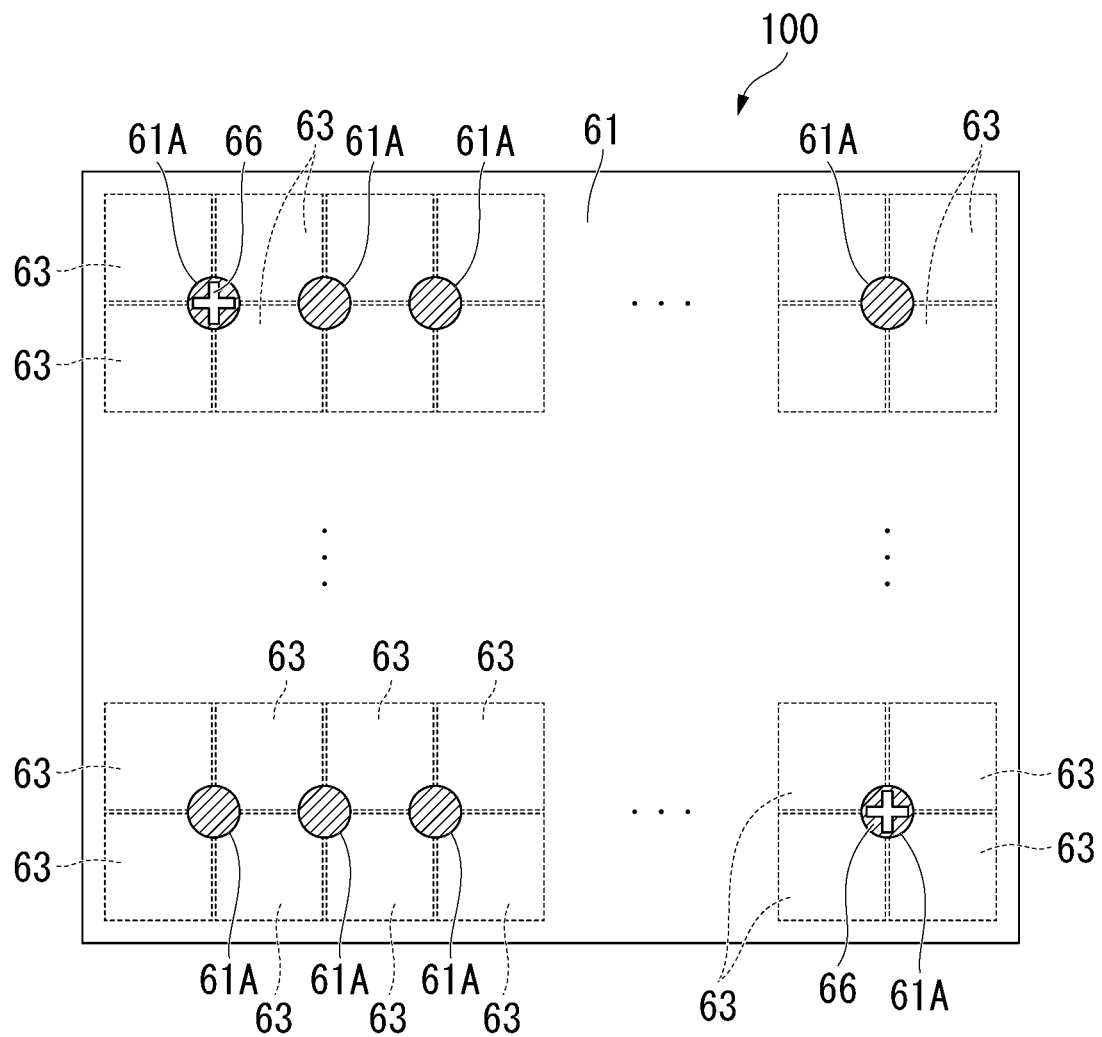
FIG. 7 is a diagram of a detector module 100 of a second embodiment when viewed from above.

Next, the second embodiment will be described. Although the through holes 61A in the first electrode 61 are provided only in two places where the marks 66 are provided in the first embodiment, the through holes 61A are provided in more places in the second embodiment. For example, the through holes 61A are provided at a plurality of positions including positions where the marks 66 can be visually recognized from the incident surface side and other positions. FIG. 7 is a view of the detector module 100 of the second embodiment when viewed from above.

The detector module 100 of the second embodiment includes a plurality of second electrodes 63 arranged in a matrix as in the first embodiment. Through holes 61A are provided at positions of the first electrode 61 corresponding to corners where four second electrodes 63 face each other in each of the plurality of second electrodes 63. Accordingly, a larger number of through holes 61A than in the first embodiment is provided.

Marks 66 are provided on the surface of the detection element 62 seen through two through holes 61A provided at the corners where the four second electrodes 63 at diagonal positions of the first electrode 61 face each other among the large number of through holes 61A. Accordingly, the first electrode 61 is provided with a larger number of through holes 61A than the number of marks 66.

The large number of through holes 61A provided in the first electrode 61 are provided corresponding to the positions of the second electrodes 63. Accordingly, the plurality of through holes 61A are arranged symmetrically on the surface of the first electrode 61, so to speak, arranged and formed in a well-balanced manner. Further, since the through holes 61A are provided at the corners where the four second electrodes 63 face each other, the area of a portion of the first electrode 61 facing the second electrodes 63 is not so small.

Figure 8:
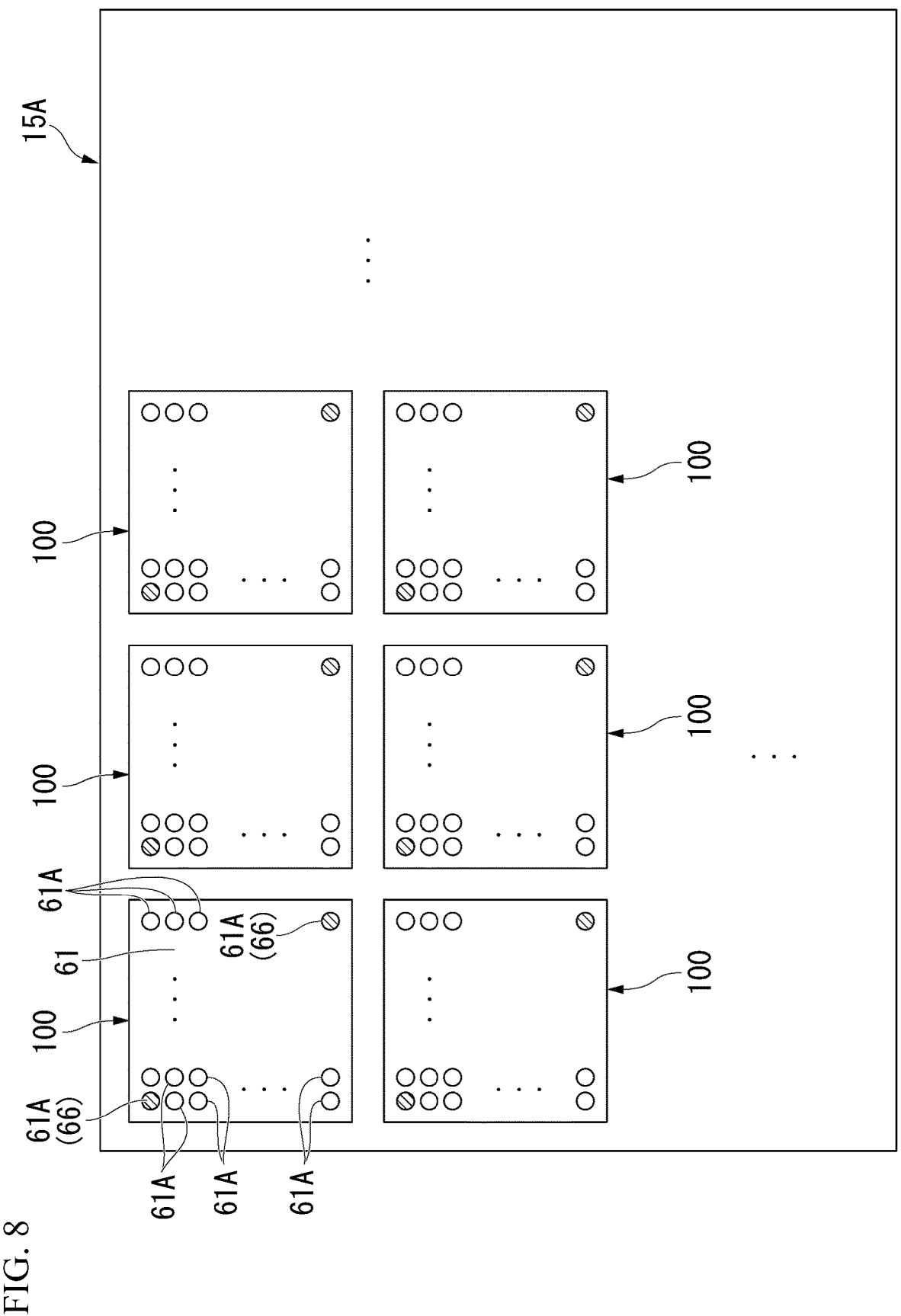
FIG. 8 is a diagram of an X-ray detector unit 15A of the second embodiment when viewed from above.

FIG. 8 is a view of the X-ray detector unit 15A of the second embodiment when viewed from above. In the X-ray detector unit 15A of the second embodiment, the plurality of detector modules 100 are each provided with marks 66 (refer to FIG. 2) at positions seen through the two through holes 61A at diagonal positions of the first electrode 61. By aligning the positions of the marks 66 seen through the through holes 61A between adjacent detector modules 100, the adjacent detector modules 100 are positioned with respect to each other.

The detector module 100 of the second embodiment has the same effect as that of the detector module 100 of the first embodiment. Further, in the detector module 100 of the second embodiment, the first electrode 61 is provided with a large number of through holes 61A corresponding to the positions of the second electrodes 63. Accordingly, a voltage is evenly applied to the second electrodes 63, in other words, evenly applied to the pixels in the first electrode 61, and thus the detection accuracy of the detection element 62 can be improved.

(Other Examples of Mark)

Figure 9A:
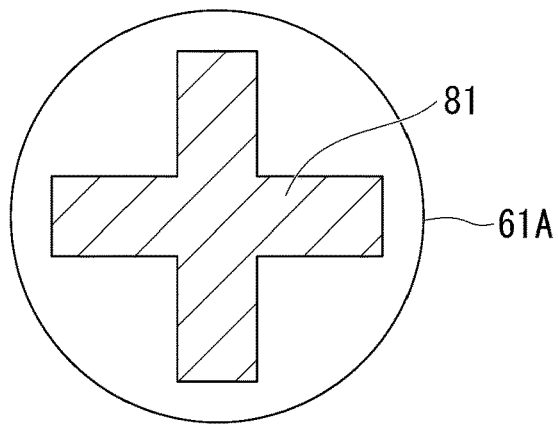
FIG. 9A is a diagram showing another example of a mark.
Figure 9B:
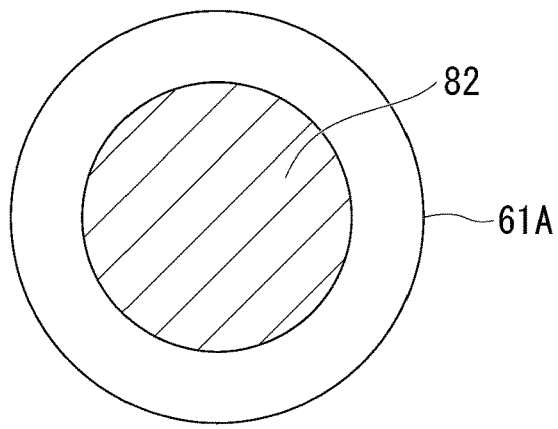
FIG. 9B is a diagram showing another example of the mark.
Figure 9C:
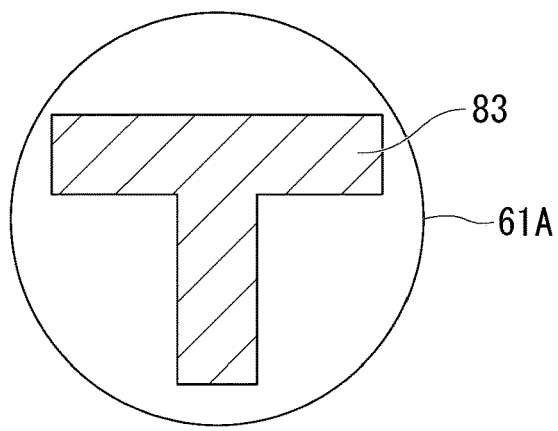
FIG. 9C is a diagram showing another example of the mark.

In each of the above embodiments, the mark 66 has a substantially cross shape but may have other shapes. FIG. 9A to FIG. 9C are views all showing other examples of marks. For example, as shown in FIG. 9A, a mark 81 is formed of the same material as the first electrode 61 or a different material on the surface of the detection element seen through the through hole 61A. In this case, the mark 81 may be formed on the surface of the detection element 62 before the first electrode 61 is formed. Further, the mark 81 may be formed by masking a portion excluding the portion to be the mark 81, or the mark 81 may be formed through etching processing.

In addition, as shown in FIG. 9B, a circular mark 82 may be formed on the surface of the detection element seen through the through hole 61A. Further, as shown in FIG. 9C, a substantially T-shaped mark 83 may be formed on the surface of the detection element seen through the through hole 61A. When the cross-shaped marks 66 and 81 and the T-shaped mark 83 are formed, the marks 66, 81, and 83 may be formed such that the direction of a straight line portion is parallel to the outside of the body in the plurality of detector modules 100.

In each of the above embodiments, the mark 66 is provided on the surface of the detection element 62. On the other hand, the mark 66 may be provided on the surface of the first electrode 61. In this case, the mark 66 may be provided at the same time when the first electrode 61 is formed by masking the place where the mark 66 will be provided and depositing a metal on the surface of the detection element 62. The mark 66 may be formed by performing etching processing after formation of the first electrode 61. The mark 66 may be provided on both the surface of the first electrode 61 and the surface of the detection element 62.

Further, although two marks 66 are provided in each of the above embodiments, a single mark 66 may be provided or three or more marks 66 may be provided. Although the mark 66 is provided at the same position between adjacent detector modules 100, the mark 66 may be provided at different positions between adjacent detector modules 100. The mark 66 may be formed of a material other than the same material as the first electrode 61. For example, the mark 66 may be provided by applying a paint or the like on the surface of the detection element 62 or the first electrode 61.

Third Embodiment

Next, the third embodiment will be described. Although the through hole 61A for allowing the mark 66 to be visually recognizable from the incident surface side is provided in the first electrode 61 in the first embodiment, a through hole that allows the mark 66 to be visually recognizable from the incident surface side is also provided in an electrode film provided on the upper side of the first electrode 61 in the third embodiment.

FIG. 10 is an enlarged view showing a part of an X-ray detector unit 15B according to the third embodiment. The X-ray detector unit 15B shown in FIG. 10 includes an electrode film 67 additionally provided on the X-ray detector unit 15A shown in FIG. 2. The electrode film 67 is provided on the upper side of the first electrode 61 of each detector module 100 included in the X-ray detector unit 15A. The electrode film 67 is conductive and has a film shape. The electrode film 67 uniformly supplies a voltage supplied from a voltage source (not shown) to the first electrode 61 of each detector module 100.

Through holes 67A are formed in the electrode film 67. At the portions where the through holes 67A are formed, parts of the surface of the detection element 62 are exposed through the through holes 61A of the first electrode 61. When the through holes 67A are viewed from above the electrode film 67, the exposed portions on the surface of the detection element 62 can be visually recognized. For example, the mark 66 as shown in FIG. 3 is provided on the exposed portions on the surface of the detection element 62.

Figure 11:
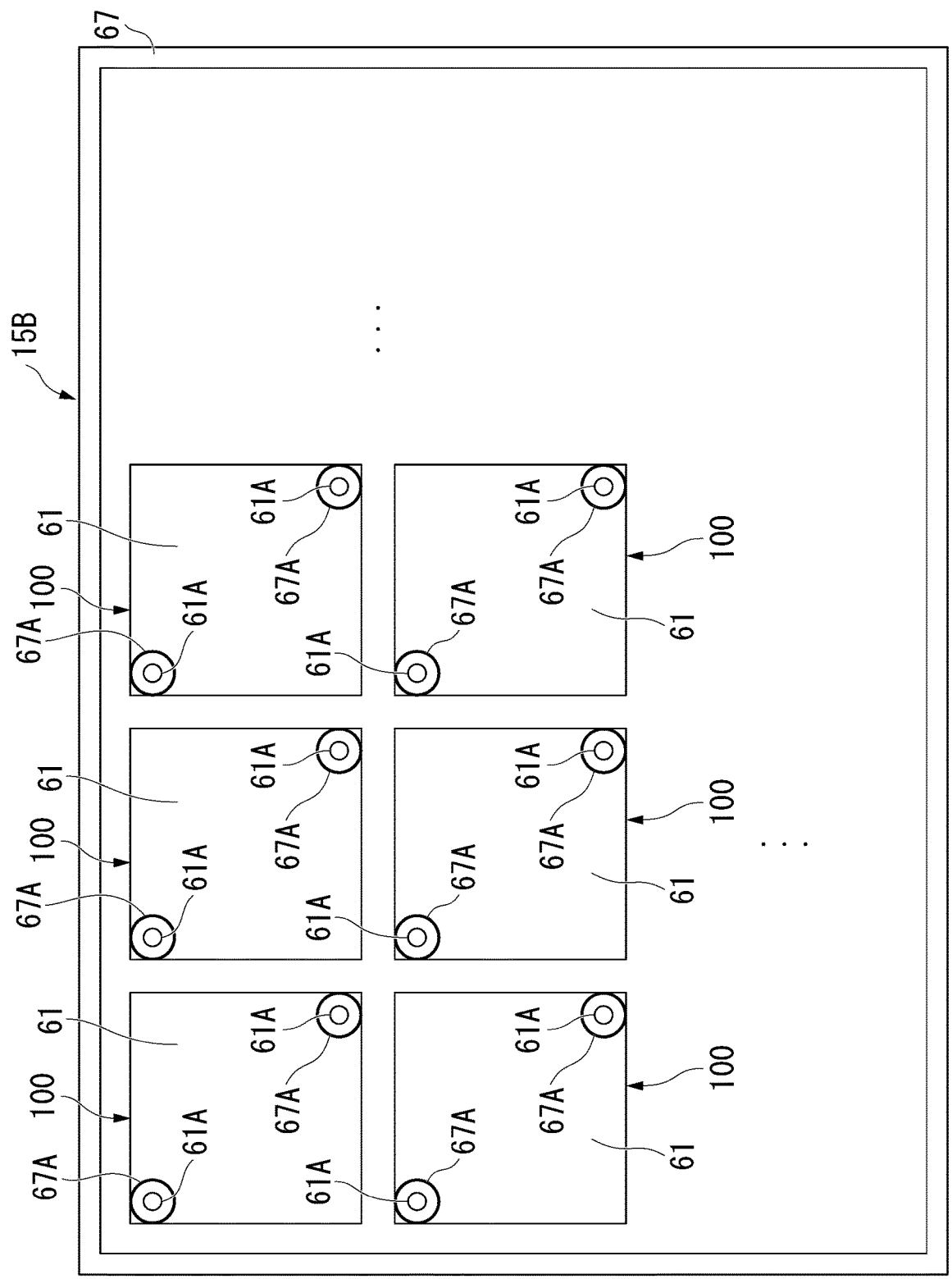
FIG. 11 is a diagram of the X-ray detector unit 15B according to the third embodiment when viewed from above.

FIG. 11 is a view of the X-ray detector unit 15B according to the third embodiment when viewed from above. A plurality of detector modules 100 are arranged side by side in the X-ray detector unit 15B. In each of the plurality of detector modules 100, two through holes 61A are formed in the first electrode 61 and the marks 66 (refer to FIG. 3) are provided at positions seen through the through holes 61A. Further, through holes 67A are provided at positions corresponding to the marks 66 of the electrode film 67. When the through holes 67A are viewed from above the electrode film 67, the marks 66 on the surface of the detection element 62 can be visually recognized through the through holes 61A of the first electrode 61. By aligning the positions of the marks 66 seen through the through holes 67A between adjacent detector modules 100, the adjacent detector modules 100 can be positioned with respect to each other.

In the X-ray detector unit 15B of the third embodiment, marks 66 for aligning pixels between adjacent detector module 100 are provided on the detection element 62. The first electrode 61 is provided with the through holes 61A that allow the marks 66 provided on the detection element 62 to be visually recognizable, and the electrode film 67 is provided with through holes 67A that allow the marks 66 provided on the detection element 62 to be visually recognizable via the through holes 61A. Accordingly, positioning is performed while viewing the marks 66, and thus the accuracy of positioning of the detector module 100 can be improved.

Fourth Embodiment

Figure 12:
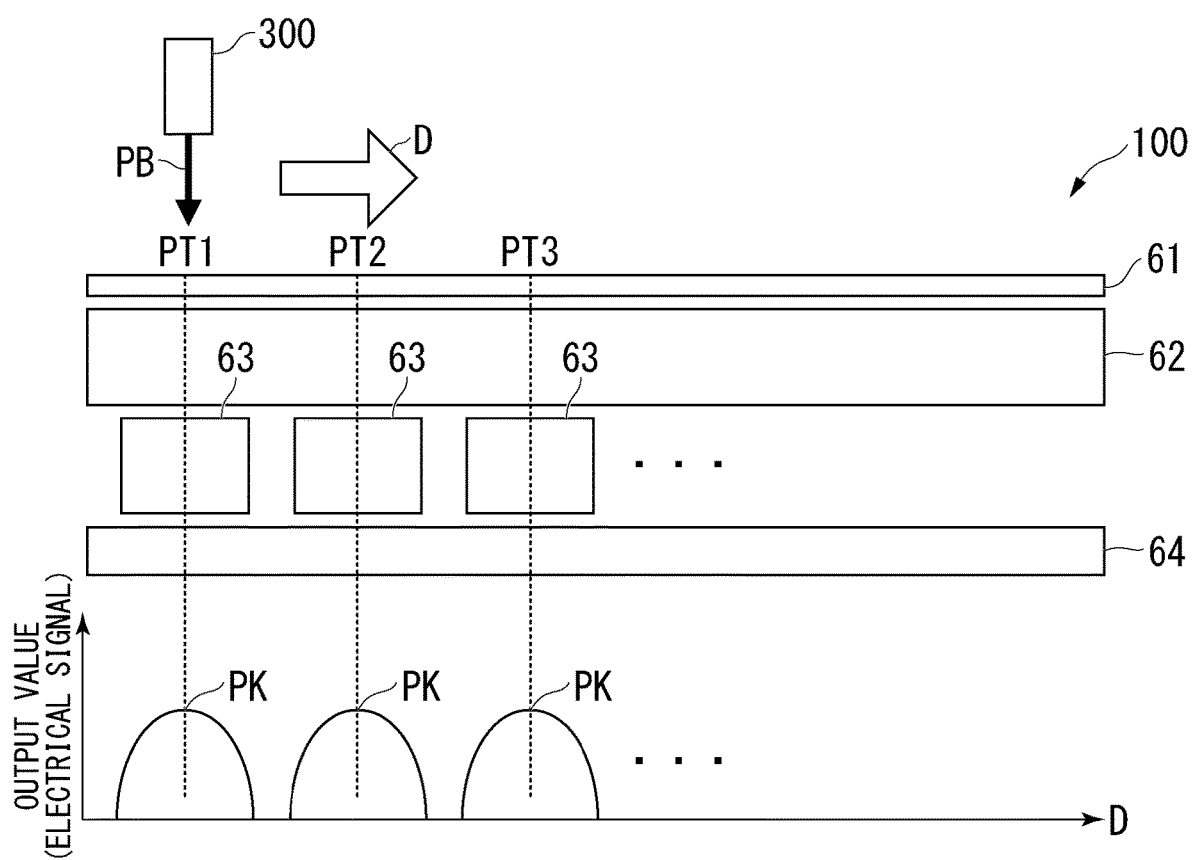
FIG. 12 is a diagram showing a state in which processing of estimating the position of each pixel is performed using a pencil beam PB according to a fourth embodiment.

Next, the fourth embodiment will be described. In the fourth embodiment, processing of estimating the position of each pixel using a pencil beam is performed at the time of positioning the detector module 100. FIG. 12 is a diagram showing a state in which processing of estimating the position of each pixel is performed using a pencil beam PB according to the fourth embodiment.

As shown in FIG. 12, an X-ray source 300 radiates the pencil beam PB (X-ray) to the detector module 100 from above the first electrode 61 of the detector module 100. At this time, radiation by the X-ray source 300 is performed while moving the radiation position of the pencil beam PB in the detector module 100 in a predetermined direction (for example, a direction D). Further, radiation by the X-ray source 300 may be performed while moving the radiation position of the pencil beam PB in the detector module 100 in a direction orthogonal to the direction D on the upper side surface of the first electrode 61. The pencil beam PB has, for example, a beam size equal to or less than the size of each pixel. The pencil beam PB may have a beam size larger than the size of each pixel.

The positions of pixels (the positions of the second electrodes 63) are estimated by observing change in an electrical signal output from the detector module 100, accompanied by change in the radiation position of the pencil beam PB. In the example shown in FIG. 12, an output value (electrical signal) of the detector module 100 shows a peak PK when radiation positions of the pencil beam PB are positions PT1, PT2, and PT3. In this case, it can be estimated that the positions PT1, PT2, and PT3 at which the output value indicates the peak PK are center positions of pixels (center positions of the second electrode 63). Such estimation processing may be performed, for example, in the processing circuitry 50 of the console device 40, and the estimation result may be output to the display 42.

In the X-ray detector unit of the fourth embodiment, the position of each pixel is estimated by using a pencil beam in order to align pixels between adjacent detector modules 100. Accordingly, the accuracy of positioning of the detector module 100 can be improved.

According to at least one embodiment described above, it is possible to improve the accuracy of positioning of the radiation detector module by including a radiation detection element that detects radiation incident from an incident surface, a first electrode provided on an incident surface side of the radiation detection element, a second electrode provided to face the first electrode having the radiation detection element interposed therebetween, and a mark provided on at least one of the incident surface of the radiation detection element and the first electrode.

Although several embodiments have been described, these embodiments are presented as examples and are not intended to limit the scope of the invention. These embodiments can be implemented in various other embodiments, and various omissions, substitutions, and modifications can be made without departing from the gist of the invention. These embodiments and variations thereof are included in the scope and gist of the invention and described in the claims and the equivalent scope thereof.

Regarding the above embodiments, the following appendices are disclosed as one aspect and selective features of the invention.

Appendix 1

A radiation detector module including:
  a radiation detection element that includes an incident surface and is configured to detect radiation incident from the incident surface;
  a first electrode provided on a side of the incident surface of the radiation detection element;
  a second electrode provided to face the first electrode through the radiation detection element; and
  a mark provided on at least one of the incident surface of the radiation detection element and the first electrode.

Appendix 2

The mark may be provided based on the position of the second electrode.

Appendix 3

The mark may be provided on the incident surface of the radiation detection element, and a through hole configured to allow the mark to be visually recognizable from the side of the incident surface may be provided on the first electrode.

Appendix 4

The through hole may be provided only at a position where the mark is visually recognizable from the side of the incident surface.

Appendix 5

The through hole may be provided at a plurality of positions including a position where the mark is visually recognizable from the side of the incident surface.

Appendix 6

A plurality of marks may be included.

Appendix 7

The mark may include the same material as the first electrode.

Appendix 8

The first electrode may be provided by depositing a material on the radiation detection element, and the mark may be provided by being masked when the first electrode is formed.

Appendix 9

The radiation detector module may be provided in a radiation detector including a plurality of radiation detector modules, and the mark may be used for positioning the second electrode and another second electrode in another adjacent radiation detector module.

Appendix 10

An electrode film provided on the side of the incident surface of the first electrode and supplying a voltage to the first electrode may be further included, and a through hole configured to allow the mark to be visually recognizable from the side of the incident surface may be provided in the electrode film.

Appendix 11

A radiation detector including the aforementioned radiation detector module.

Appendix 12

An X-ray CT apparatus including the radiation detector, wherein the radiation is X-rays.

Appendix 13

The through hole provided in the electrode film may be configured to allow mark to be visually recognizable from the side of the incident surface through the through hole provided in the first electrode.

Appendix 14

The mark and the through hole of the first electrode may be provided at positions corresponding to corners where four second electrodes among a plurality of second electrodes arranged in a matrix face each other.

Appendix 15

The first electrode may be provided by depositing a material on the radiation detection element, and the mark may be provided by being masked when the first electrode is formed to form a bordering portion for bordering the mark.

Appendix 16

The mark may have any of a cross shape, a circular shape, and a T-shape.

What is claimed is:

1. A radiation detector module, comprising:
    a radiation detection element that includes an incident surface and is configured to detect radiation incident from the incident surface;
    a first electrode provided on a side of the incident surface of the radiation detection element;
    a second electrode provided to face the first electrode through the radiation detection element; and
    a mark provided on the incident surface of the radiation detection element,
    wherein a through hole is provided on the first electrode, the through hole being placed at a position where the mark, which is provided on the incident surface of the radiation detection element under the first electrode, is visually recognizable via the through hole when viewed from the side of the incident surface.

2. The radiation detector module according to claim 1, wherein the mark is provided based on a position of the second electrode.

3. The radiation detector module according to claim 1, wherein the through hole is provided only at a position where the mark is visually recognizable from the side of the incident surface.

4. The radiation detector module according to claim 1, wherein the through hole is provided at a plurality of positions including a position where the mark is visually recognizable from the side of the incident surface.

5. The radiation detector module according to claim 1, comprising a plurality of marks.

6. The radiation detector module according to claim 1, wherein the mark includes a same material as the first electrode.

7. The radiation detector module according to claim 1, wherein the first electrode is provided by depositing a material on the radiation detection element, and the mark is provided by being masked when the first electrode is formed.

8. The radiation detector module according to claim 1, wherein the radiation detector module is provided in a radiation detector including a plurality of radiation detector modules, and
    the mark is for positioning the second electrode and another second electrode in another adjacent radiation detector module.

9. The radiation detector module according to claim 1, further comprising an electrode film provided on the side of the incident surface of the first electrode and supplying a voltage to the first electrode,
    wherein the through hole, which is configured to allow the mark to be visually recognizable from the side of the incident surface is provided in the electrode film.

10. A radiation detector comprising the radiation detector module according to claim 1.

11. An X-ray CT apparatus comprising the radiation detector according to claim 10, wherein the radiation is X-rays.

\* \* \* \* \*